US008592779B2

(12) United States Patent
Matsuura et al.

(10) Patent No.: US 8,592,779 B2
(45) Date of Patent: Nov. 26, 2013

(54) IONIZING DEVICE

(75) Inventors: Shigeki Matsuura, Hamamatsu (JP);
Yoshihiro Takata, Tachikawa (JP);
Tadashi Arii, Fussa (JP); Satoshi Otake,
Ome (JP)

(73) Assignees: Hamamatsu Photonics K.K.,
Hamamatsu-shi, Shizuoka (JP); Rigaku Corporation, Akishima-shi, Tokyo (JP)

( * ) Notice: Subject to any disclaimer, the term of this patent is extended or adjusted under 35 U.S.C. 154(b) by 884 days.

(21) Appl. No.: 12/281,069

(22) PCT Filed: Mar. 16, 2007

(86) PCT No.: PCT/JP2007/055367
§ 371 (c)(1),
(2), (4) Date: Sep. 5, 2008

(87) PCT Pub. No.: WO2007/108410
PCT Pub. Date: Sep. 27, 2007

(65) Prior Publication Data
US 2009/0008571 A1    Jan. 8, 2009

(30) Foreign Application Priority Data
Mar. 17, 2006  (JP) .............................. P2006-075012

(51) Int. Cl.
*H01J 27/00*   (2006.01)
(52) U.S. Cl.
USPC ................... 250/427; 250/423 R; 250/423 P; 250/424
(58) Field of Classification Search
None
See application file for complete search history.

(56) References Cited

U.S. PATENT DOCUMENTS

| | | | | |
|---|---|---|---|---|
| 4,476,392 A | * | 10/1984 | Young | 250/423 R |
| 4,855,594 A | | 8/1989 | Kimock et al. | |
| 5,206,594 A | * | 4/1993 | Zipf | 324/464 |
| 5,294,797 A | | 3/1994 | Frey et al. | |
| 5,561,344 A | * | 10/1996 | Hsi | 313/494 |
| 5,629,518 A | | 5/1997 | Grotheer et al. | |
| 6,329,653 B1 | | 12/2001 | Syage et al. | |
| 6,967,485 B1 | * | 11/2005 | Hsueh et al. | 324/464 |
| 7,279,680 B2 | | 10/2007 | Miller et al. | |
| 2002/0125425 A1 | | 9/2002 | Kato | |
| 2003/0020014 A1 | | 1/2003 | Zimmermann et al. | |
| 2006/0043279 A1 | * | 3/2006 | Kudryavtsev et al. | 250/282 |

(Continued)

FOREIGN PATENT DOCUMENTS

| | | | |
|---|---|---|---|
| JP | 54076198 A | * | 6/1979 |
| JP | 60-157017 | | 8/1985 |

(Continued)

OTHER PUBLICATIONS

PCT/ISA/210 of International Application No. PCT/JP2007/000238.

(Continued)

*Primary Examiner* — Andrew Smyth
(74) *Attorney, Agent, or Firm* — Drinker Biddle & Reath LLP

(57) ABSTRACT

An ionizing device 2 includes an ionization chamber 2*a* having an ionization space 2*b* for ionizing sample molecules A, filaments 23*a* and 23*b* to have an electron impact on the sample molecules A in the ionization space 2*b*, to ionize the sample molecules A, and an electric discharge tube 29 to irradiate the sample molecules A in the ionization space 2*b* with ultraviolet light, to ionize the sample molecules A.

23 Claims, 9 Drawing Sheets

(56) References Cited

U.S. PATENT DOCUMENTS

| | | |
|---|---|---|
| 2006/0284075 A1 | 12/2006 | Bonne et al. |
| 2009/0026362 A1 | 1/2009 | Arii et al. |
| 2009/0218482 A1 | 9/2009 | Muehlberger et al. |

FOREIGN PATENT DOCUMENTS

| | | | |
|---|---|---|---|
| JP | 60157017 A | * | 8/1985 |
| JP | 63-55846 | | 3/1988 |
| JP | 2-176459 | | 7/1990 |
| JP | 02176459 A | * | 7/1990 |
| JP | 3-102757 | | 4/1991 |
| JP | 03102757 A | * | 4/1991 |
| JP | 3-171544 | | 7/1991 |
| JP | 04152296 A | * | 5/1992 |
| JP | 4-296433 | | 10/1992 |
| JP | 04-371571 | | 12/1992 |
| JP | 05-106029 | | 4/1993 |
| JP | 05106029 A | * | 4/1993 |
| JP | 06045092 A | * | 2/1994 |
| JP | 8-30695 | | 3/1996 |
| JP | 09068473 A | * | 3/1997 |
| JP | 11-64284 | | 3/1999 |
| JP | 11064284 A | * | 3/1999 |
| JP | 2000-357488 | | 12/2000 |
| JP | 2001-273869 | | 10/2001 |
| JP | 2003-279543 A | | 10/2003 |
| JP | 2004-502136 | | 1/2004 |
| JP | 2004-356073 | | 12/2004 |
| JP | 2005-004989 | | 1/2005 |
| JP | 2005-005128 | | 1/2005 |
| JP | 2005-93152 | | 4/2005 |
| WO | WO-01/73816 | | 10/2001 |
| WO | WO-2005/013341 | | 2/2005 |
| WO | WO 2007/019982 | | 2/2007 |

OTHER PUBLICATIONS

PCT/ISA/237 of International Application No. PCT/JP2007/000238.

* cited by examiner

IONIZING DEVICE

TECHNICAL FIELD

The present invention relates to an ionizing device.

BACKGROUND ART

For example, as a method for ionizing sample molecules such as an organic material, there is an electron-impact ionization technique (EI: Electron impact Ionization) in which an impact is made on sample molecules by using accelerated electrons so as to ionize the sample molecules, and a photo-ionization technique (PI: Photo Ionization) in which sample molecules are exposed to light to be ionized. A mass analyzer described in Patent Document 1 includes a filament that generates thermal electrons for EI and a laser light source that generates a laser light for PI.

Patent Document 1: Japanese Unexamined Patent Application Publication No. 2005-93152

DISCLOSURE OF THE INVENTION

Problems to be Solved by the Invention

In many cases, sample molecules are introduced as a gas, or introduced along with a carrier gas. Then, in order to improve the detection efficiency and detection sensitivity, it is preferable that an ionizable region is wider, and in PI, it is preferable that a gas introduced over a wide range is uniformly exposed to light. However, in the mass analyzer described in Patent Document 1, because a laser light is used for PI, an irradiated range is narrow, and an ionizable region also is narrow, which makes it difficult to improve the detection efficiency and detection sensitivity. Further, in order to expand an irradiated range, there are also methods by using a beam expander or the like or in which a laser light source is scanning-operated. However, not only does a laser light source itself bring about an increase in the size of the device, but also a beam expander or a scanning operation mechanism brings about a further increase in the size of the device.

The present invention has been achieved in consideration of the above-described problems, and an object of the invention is to provide an ionizing device which is capable of performing both EI and PI, and also can be made compact, and which is capable of improving the detection efficiency and detection sensitivity by radiating light on sample molecules uniformly over a wide range in PI.

Means for Solving the Problems

In order to solve the above-described problems, the ionizing device of the present invention includes an ionization chamber having an ionization space for ionizing sample molecules, an electron source to have an electron impact on the sample molecules in the ionization space, to ionize the sample molecules, and a light emission means for irradiating the sample molecules in the ionization space with ultraviolet light whose directivity is lower than that of a laser light, to ionize the sample molecules.

The ionizing device described above is capable of both EI and PI by including the electron source and the light emission means that radiates ultraviolet light whose directivity is lower than that of a laser light. Moreover, because the ionizing device radiates ultraviolet light whose directivity is lower than that of a laser light, the ionizing device is capable of irradiating the sample molecules introduced in a wider range uniformly with ultraviolet light. In accordance therewith, it is possible to improve the detection efficiency and detection sensitivity.

Further, in the ionizing device, the light emission means may be an electric discharge tube. By using an electric discharge tube as the light emission means, the ionizing device can be formed more compact as compared with an ultraviolet laser light source.

Further, the ionizing device may further have a first accelerating electrode, which is disposed between the electron source and the ionization space, to accelerate electrons from the electron source toward the ionization space. In accordance therewith, it is possible to suitably accelerate electrons emitted from the electron source, and effectively have an electron impact on the sample molecules.

Further, the ionizing device may further have an electron collecting electrode, which is disposed outside the ionization space, to collect electrons generated due to the ultraviolet light irradiation in the ionization space. When the interior of the ionization chamber is irradiated with ultraviolet light, secondary electrons are emitted from structural members such as an electron and the like due to the photo-electric effect. Then, when the secondary electrons penetrate into the ionization space, the secondary electrons have an electron impact on the sample molecules. Originally, PI is a method suitable for generating molecular ions (parent ions) of the sample molecules, which are decomposed into fragment ions due to too high ionization energy in EI. However, some of the sample molecules are changed into fragment ions in EI by the secondary electrons as described above. In accordance with the ionizing device described above, provided that the electron collecting electrode to collect electrons (secondary electrons) generated due to ultraviolet light irradiation in the ionization chamber, is provided outside the ionization space, it is possible to prevent the secondary electrons from penetrating into the ionization space, and reduce the emergence of fragment ions in PI.

Further, the ionizing device may further have a second accelerating electrode, which is disposed between the electron collecting electrode and the ionization space, to accelerate electrons generated due to the ultraviolet light irradiation in the ionization space toward the electron collecting electrode. In accordance therewith, it is possible to more effectively prevent the secondary electrons from penetrating into the ionization space. Further, in this case, it is preferable that the ionizing device has a first accelerating electrode, which is disposed between the electron source and the ionization space, to accelerate electrons from the electron source toward the ionization space, and the first accelerating electrode serves as the second accelerating electrode. In accordance therewith, because the ionizing device can be composed of fewer members, it is possible to prevent the device from being increased in size.

Further, in the ionizing device, the electron source may include an electron emitting electrode that emits electrons due to the ultraviolet light irradiation from the light emission means. As an electron source for EI, there is a filament and the like for example. However, an electron emitting electrode that emits electrons (secondary elections) by receiving ultraviolet light in this way is capable of suitably emitting electrons for EI.

Further, in the ionizing device, the electron emitting electrode may have a base portion and a coating portion that coats the base portion, and a secondary electron emission efficiency of the coating portion may be higher than a secondary electron emission efficiency of the base portion. In this way, by providing the coating portion having a high secondary electron emission efficiency to the electron emitting electrode, it is possible to more efficiently emit electrons for EI.

Further, the ionizing device of the present invention includes an ionization chamber having an ionization space for ionizing sample molecules, a light emission means for irradiating the sample molecules in the ionization space with ultraviolet light whose directivity is lower than that of a laser light, to ionize the sample molecules, a first electrode which is disposed outside the ionization space, the first electrode performs an electron emitting operation for emitting electrons due to the ultraviolet light irradiation from the light emission means to have an electron impact on the sample molecules in the ionization space, and an electron collecting operation for collecting electrons generated in the ionization chamber due to the ultraviolet light irradiation, and a second electrode which is disposed between the first electrode and the ionization space, and in the ionizing device, the electron emitting operation and the electron collecting operation in the first electrode are switched in accordance with a relationship between electric potentials of the first electrode and the second electrode.

The above-described ionizing device includes a light emission means that irradiates the sample molecules with ultraviolet light whose directivity is lower than that of a laser light, and a first electrode that emits electrons due to the ultraviolet light irradiation from the light emission means. In accordance therewith, both EI and PI are possible. Further, because the light emission means that radiates ultraviolet light whose directivity is lower than that of a laser light is capable of irradiating the sample molecules introduced in a wider range uniformly with ultraviolet light, it is possible to improve the detection efficiency and detection sensitivity.

Moreover, by providing the first and second electrodes, and switching the electron emitting operation and the electron collecting operation described above in accordance with a relationship between electric potentials of the first electrode and the second electrode, it is possible to effectively have an electron impact on the sample molecules in the ionization space in EI (electron emitting operation), and it is possible to prevent the secondary electrons from penetrating into the ionization space in PI, and reduce the emergence of fragment ions (electron collecting operation). In this way, because both the electron emitting operation and the electron collecting operation are possible by the first electrode, the ionizing device capable of efficiently performing both PI and EI can be made more compact.

Further, in the ionizing device, the light emission means may be an electric discharge tube. By using an electric discharge tube as the light emission means, the ionizing device can be made compact.

Further, in the ionizing device, the electron emitting operation and the electron collecting operation in the first electrode may be alternately performed while controlling operating times of the respective operations. In accordance therewith, even if the sample molecules have a time variation, molecular ions in PI and fragment ions in EI can be obtained by the same measurement taking into consideration the effect of the time variation.

Further, the ionizing device may further have a rectifier member that rectifies the sample molecules toward the ionization space. In accordance therewith, the utilization efficiency of the sample molecules is improved, which makes it possible to generate more ions.

Effects of the Invention

In accordance with the present invention, it is possible to provide an ionizing device which is capable of both EI and PI, and can be made compact, and is capable of improving the detection efficiency and detection sensitivity by irradiating sample molecules with light uniformly over a wide range in PI.

Figure 1:
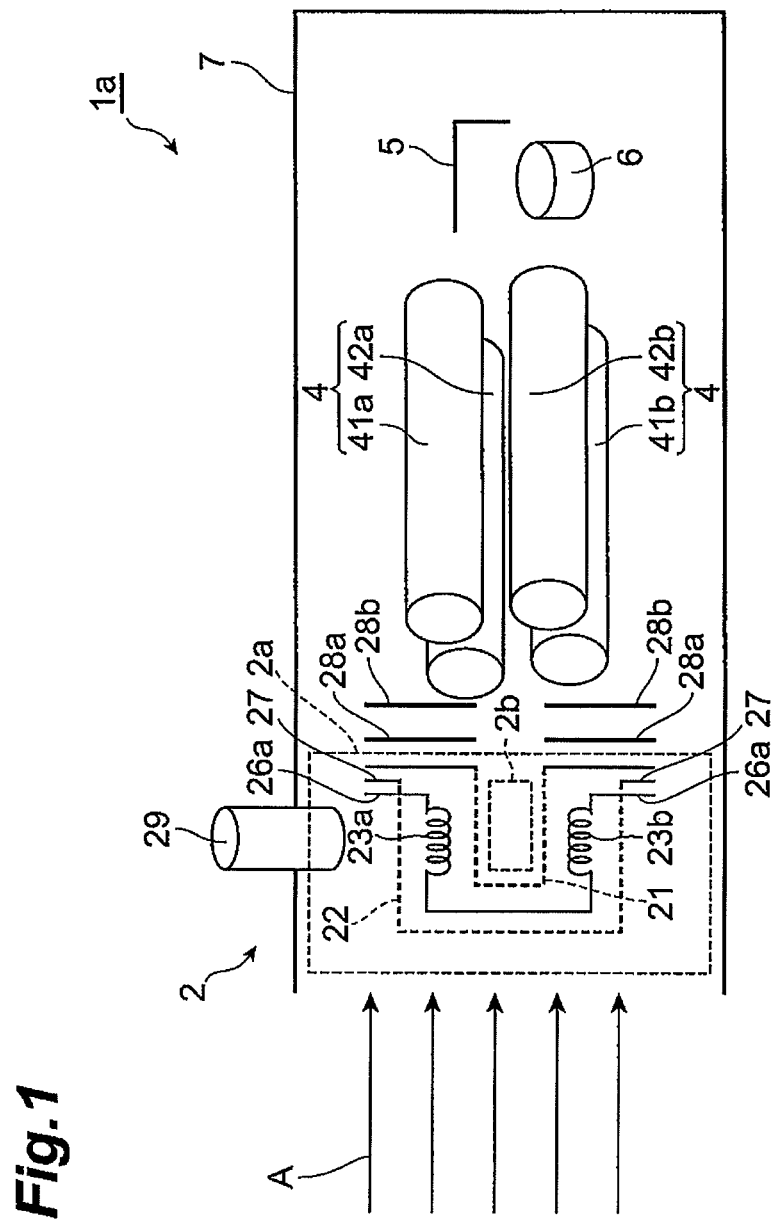
FIG. 1 is a schematic diagram showing a structure of one embodiment of an ionizing device according to the present invention, and a structure of a mass analyzer having the ionizing device.

DESCRIPTION OF THE REFERENCE NUMERALS 1a to 1c Mass analyzer
2, 2c, 2d, 8a, 8b Ionizing device
2a, 9a Ionization chamber
2b Ionization space
4 Quadrupole
5 Deflector
6 Detector
7, 9 Case
8b Ionizing device
10 Skimmer
12 Rectifier member
21, 81 Internal electrode
22, 82, 84 External electrode
23a, 23b, 86 Filament
29, 89 Electric discharge tube
85 Collector electrode
A Sample molecules
$e_A$ Thermal electrons
$e_B$ Secondary electrons
$I_A$ Fragment ions
$I_B$ Molecular ions

BEST MODES FOR CARRYING OUT THE INVENTION

Hereinafter, a preferred embodiment of an ionizing device according to the present invention will be described in detail with reference to the drawings. Note that portions which are the same as or correspond to those in the explanation of the drawings are denoted by the same reference numerals, and overlapping descriptions thereof will be omitted.

FIG. 1 is a schematic diagram showing a structure of an ionizing device 2 according to one embodiment of the ionizing device according to the present invention, and a structure of a mass analyzer 1a having the ionizing device 2. The mass analyzer 1a of the present embodiment is a device to analyze sample molecules A such as an organic matter which is introduced from the outside, and includes a quadrupole 4, a deflector 5, a detector 6, and a case 7 in addition to the ionizing device 2. The case 7 is a container capable of retaining a vacuum atmosphere, and contains the ionizing device 2, the quadrupole 4, the deflector 5, and the detector 6.

The ionizing device 2 includes an ionization chamber 2a, electron lens forming electrodes 28a and 28b, and an electric discharge tube 29. The ionization chamber 2a has an ionization space 2b for ionizing the sample molecules A, and is disposed in the vicinity of a sample introduction port in the mass analyzer 1a. The electron lens forming electrodes 28a and 28b are components to introduce ions generated in the ionization space 2b to the quadrupole 4. The electric discharge tube 29 serving as a light emission means whose directivity is lower than that of a laser light is a component to irradiate the sample molecules A introduced into the ionization space 2b with ultraviolet light (including vacuum-ultraviolet light) to ionize the sample molecules A (PI). As this electric discharge tube 29, for example, a deuterium lamp, an excimer lamp, a capillary electric discharge tube, a microwave electric discharge tube, or the like which is capable of irradiating a relatively wide range with ultraviolet light is preferably used. In the present embodiment, from the standpoint that there is less change in a quantity of ultraviolet light, a deuterium lamp excellent in its quantitative capability of data to be obtained is used.

The ionization chamber 2a flier has an internal electrode (a second electrode) 21, an external electrode (a first electrode) 22, and filaments 23a and 23b. The filaments 23a and 23b are electron sources to have an electron impact on the sample molecules A in the ionization space 2b to ionize the sample molecules A (EI). The filaments 23a and 23b are supplied with electric power from the outside of the ionizing device 2 via conductive wires 26a and 26b, and emit thermal electrons into the ionization space 2b. The filaments 23a and 23b are disposed outside the ionization space 2b.

The external electrode 22 is an electron collecting electrode to collect secondary electrons generated due to ultraviolet light irradiation in the ionization chamber 2a when it is not desired to ionize the sample molecules A by an electron impact at the time of ultraviolet light irradiation. When the interior of the ionization chamber is irradiated with ultraviolet light, secondary electrons are emitted from structural members such as the internal electrode 21, the filaments 23a and 23b, and the like. The external electrode 22 collects the secondary electrodes generated in this way. The external electrode 22 is disposed outside the filaments 23a and 23b outside the ionization space 2b. The external electrode 22 is electrically connected to the outside of the ionizing device 2 via a conductive material 27, and sends the collected secondary electrodes to the outside of the ionizing device 2.

Further, the external electrode 22 serves as an electron emitting electrode emitting secondary electrons due to ultraviolet light irradiation from the electric discharge tube 29 when it is desired to ionize the sample molecules A by an electron impact at the time of ultraviolet light irradiation. That is, as electrons for having an electron impact on the sample molecules A, not only thermal electrons from the filaments 23a and 23b, but also secondary electrons generated from structural members such as the external electrode 22, the filaments 23a and 23b, and the like due to ultraviolet light irradiation can be used. When only PI is performed for the sample molecules A, it is preferable that the secondary electrons are eliminated from the ionization space 2b as described above. However, when both PI and EI are performed for the sample molecules A, in contrast thereto, it is recommended that secondary electrons be supplied to the ionization space 2b. Due to the electron emitting electrodes (the external electrode 22 and the filaments 23a and 23b) emitting secondary electrons, it is possible to supply more electrons to the ionization space 2b. Note that, among the electron emitting electrodes, the external electrode 22 preferably has a base portion to mainly secure conductivity and a coating portion that coats the base portion and has a secondary electron emission efficiency higher than that of the base portion. In accordance therewith, it is possible to emit secondary electrons more efficiently. As a material of the coating portion whose secondary electron emission efficiency is high, for example, gold, nickel, magnesium oxide, or the like is preferable.

The internal electrode 21 is an electrode serving as both a first accelerating electrode to accelerate thermal electrons emitted from the filaments 23a and 23b or secondary electrons generated due to ultraviolet light irradiation toward the ionization space 2b when it is desired to ionize the sample molecules A by an electron impact, and a second accelerating electrode to accelerate secondary electrons generated due to ultraviolet light irradiation in the ionization space 2a toward the external electrode 22 when it is not desired to ionize the sample molecules A by an electron impact at the time of ultraviolet light irradiation. The internal electrode 21 is disposed between the filaments 23a and 23b and the external electrode 22 and the ionization space 2b. The internal electrode 21 is formed net-like or into a shape having openings for example, so as to allow the sample molecules A, thermal electrons, and secondary electrons going toward the ionization space 2b to pass through it. The internal electrode 21 is supplied with a voltage from the outside of the ionizing device 2. When the internal electrode 21 accelerates thermal electrons from the filaments 23a and 23b and secondary electrons from the filaments 23a and 23b and the external electrode 22 toward the ionization space 2b, the internal electrode 21 is kept at an electric potential higher than those of the filaments 23a and 23b and the external electrode 22. Further, when the internal electrode 21 accelerates the secondary electrons generated in the ionization chamber 2a toward the external electrode 22, the internal electrode 21 is kept at an electric potential lower than that of the external electrode 22.

The quadrupole 4 is a portion to selectively take out only ions having a specific mass/charge ratio among ions emitted from the ionizing device 2. The quadrupole 4 is composed of a pair of juxtaposed bar electrodes 41a and 41b and another pair of bar electrodes 42a and 42b, which are arranged such that the both juxtaposed directions intersect one another. By applying a voltage satisfying a certain condition (a voltage in which a direct voltage and an alternating voltage are superimposed) to the respective bar electrodes 41a, 41b, 42a, and 42b, only ions having a mass/charge ratio corresponding to the voltage condition are allowed to pass through the respective bar electrodes 41a, 41b, 42a, and 42b.

The deflector 5 is a component to change a traveling direction of the ions passing through the quadrupole 4 to the detector 6, and is disposed at the subsequent stage of the quadrupole 4. Further, the detector 6 is a component to detect the ions passing through the quadrupole 4, and generates electric current according to the number of ions.

Figure 2:
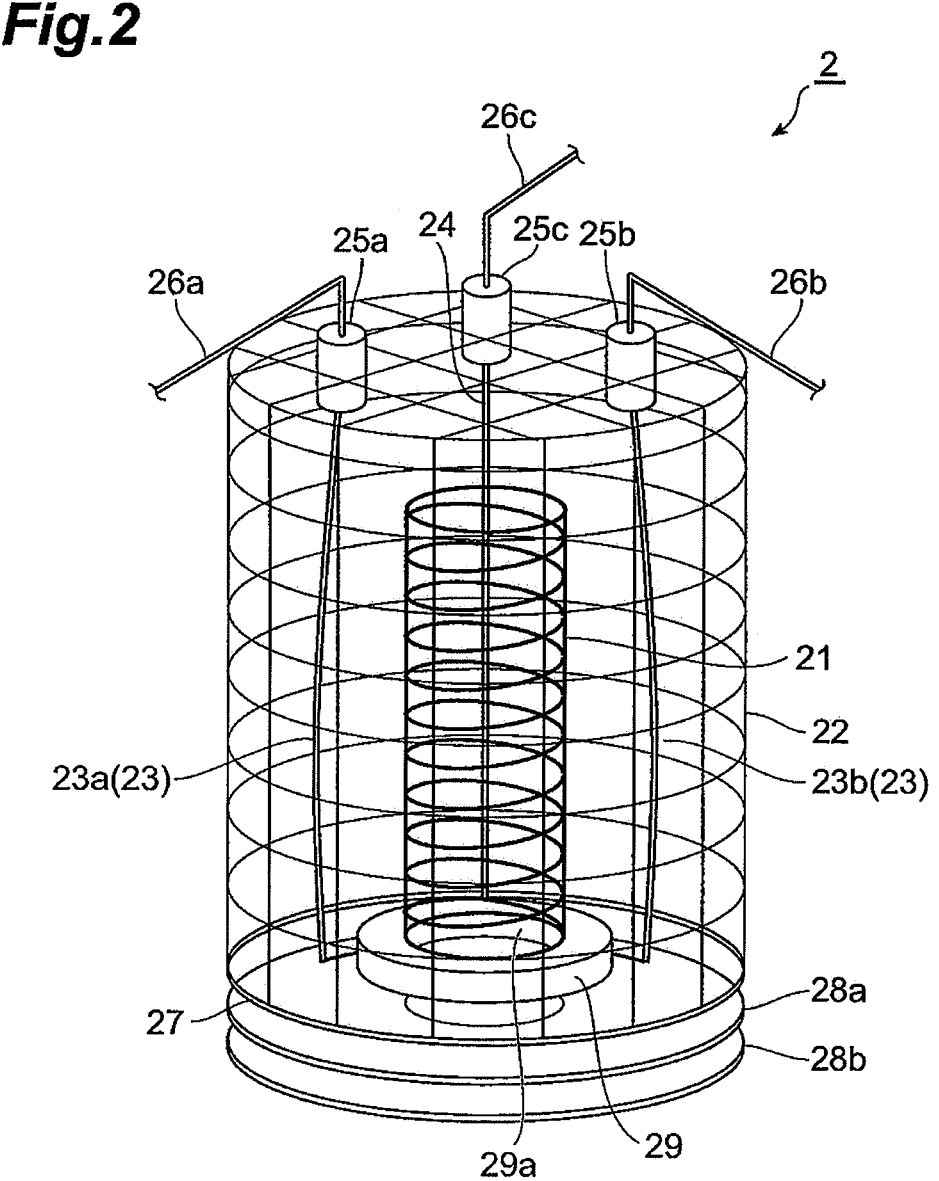
FIG. 2 is a perspective view showing the structure of the ionizing device in detail.

FIG. 2 is a perspective view showing the structure of the ionizing device 2 according to the present embodiment in detail. Note that, in FIG. 2, illustrations of the ionization chamber 2a and the electric discharge tube 29 are omitted.

The external electrode 22 of the present embodiment is formed such that conductive wires are braided net-like. The external electrode 22 is disposed so as to surround the internal electrode 21, and is formed into a cylindrical shape (basket shape) along a certain central axis. One end of the external electrode 22 is closed such that the conductive wires are braided net-like, and the cylindrical ring-shaped external conductive material 27 is fixed to the other end, and a predetermined voltage is applied thereto via conductive wires (not shown) connected to the external conductive material 27.

Further, the internal electrode 21 is formed such that a conductive wire is wound spirally, and is formed into a cylindrical shape along the same central axis as the external electrode 22. Then, the inside of the cylindrical internal electrode 21 serves as an ionization space 2b (FIG. 1). One end of the internal electrode 21 is fixed to a cylindrical ring-shaped internal conductive material 29, and a predetermined voltage is applied thereto via conductive wires (not shown) connected to the internal conductive material 29. An opening 29a is formed in a portion of the internal conductive material 29 corresponding to the internal electrode 21, and ions generated in the ionization space 2b pass through the opening 29a to be taken out to the side of the electron lens forming electrodes 28a and 28b.

The filaments 23a and 23b are disposed between the internal electrode 21 and the external electrode 22, and extend along the central axis of the internal electrode 21 and the external electrode 22. One ends of the filaments 23a and 23b are electrically connected to the outside of the ionizing device 2 (for example, a power supply terminal of a power supply unit) via the conductive wires 26a and 26b disposed outside the external electrode 22. Further, the other ends of the filaments 23a and 23b are electrically connected to one end of a conductive wire 24 disposed between the internal electrode 21 and the external electrode 22. The other end of the conductive wire 24 is electrically connected to the outside of the ionizing device 2 (for example, the power ground terminal of the power supply unit) via a conductive wire 26c disposed outside the external electrode 22. Note that the conductive wires 26a to 26c and the external electrode 22 are insulated from one another with insulating materials 25a to 25c.

The electron lens forming electrodes 28a and 28b are disposed at the back side of the disc-like conductive material 27 (an opposite side of the side at the external electrode 22 is provided). The electron lens forming electrodes 28a and 28b are disposed so as to be arrayed in a direction of the central axis of the internal electrode 21 and the external electrode 22, and are formed in a disk shape centering on the central axis. Further, the electron lens forming electrodes 28a and 28b respectively have openings that communicate with one another to allow the ionized sample molecules A to pass through those. By applying a predetermined voltage to those, the electron lens forming electrodes 28a and 28b form an electric field by which ions are pulled out of the ionization space 2b toward the quadrupole 4.

The operations of the ionizing device 2 having the above-described structure (an EI operation by the filaments 23a and 23b, a PI operation by the electric discharge tube 29, and an EI operation by the electric discharge tube 29) will be described. Note that, in the respective operations, first, the sample molecules A are taken into the ionizing device 2. Thereafter, the sample molecules A pass through the external electrode 22 and the internal electrode 21, and are introduced into the ionization space 2b. At this time, a substance which is the sample molecules A is taken into the ionizing device 2 singularly as the substance in some cases, or is taken into the ionizing device 2 along with a carrier gas such as nitrogen gas in some cases.

[EI Operation by the Filaments 23a and 23b]

Figure 3:
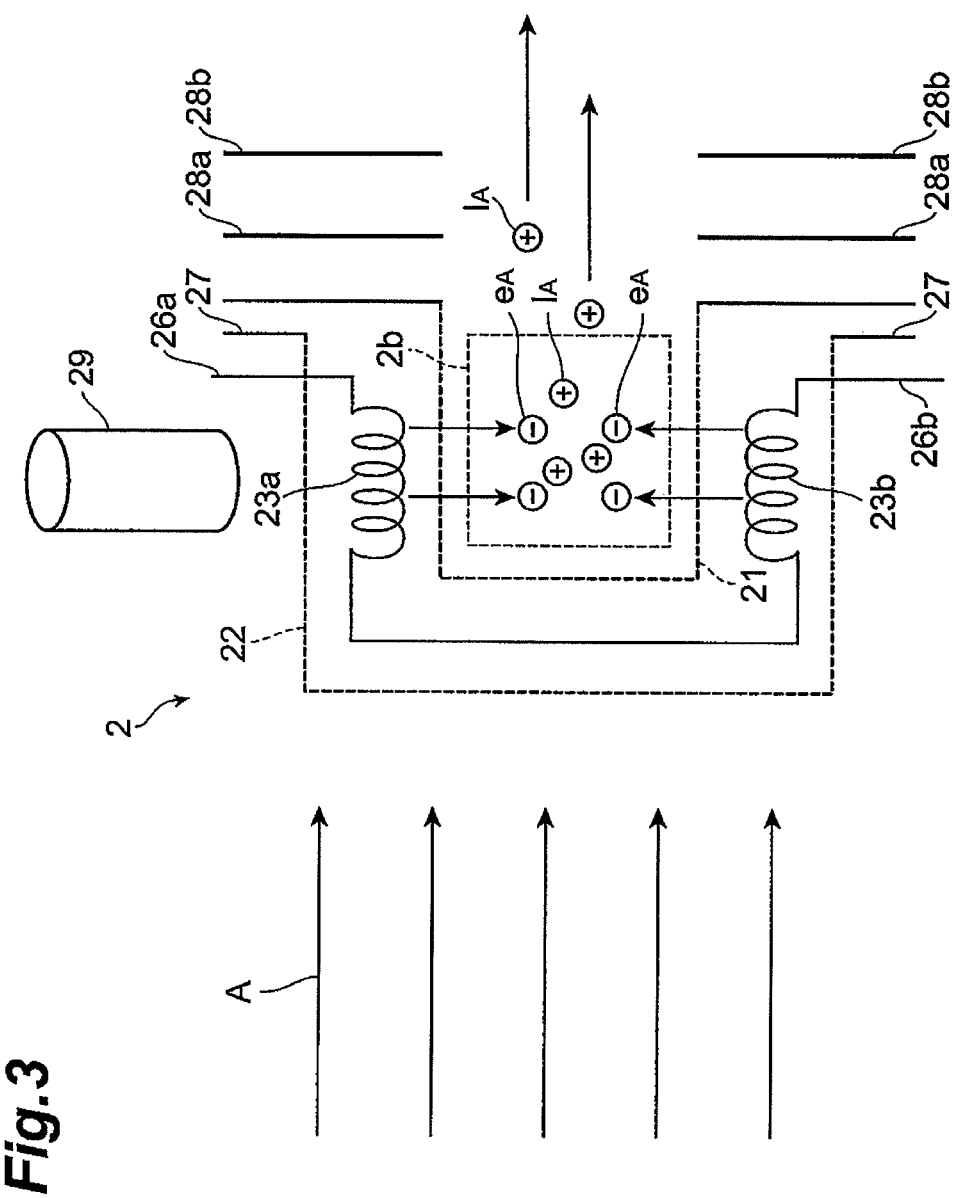
FIG. 3 is a diagram for explanation of an EI operation by filaments among the operations of the ionizing device.

FIG. 3 is a diagram for explanation of an EI operation by the filaments 23a and 23b among the operations of the ionizing device 2. In an EI operation, the filaments 23a and 23b are supplied with electric power via the conductive wires 26a and 26b, and emit thermal electrons $e_A$. At this time, an electric potential V1 of the internal electrode 21, an electric potential V2 of the external electrode 22, and an electric potential V3 of the filaments 23a and 23b satisfy the relationship of V1>V3≥V2. Accordingly, the thermal electrons $e_A$ are accelerated by the electric field formed between the internal electrode 21 and the filaments 23a and 23b (between the internal electrode 21 and the external electrode 22), and the thermal electrons $e_A$ pass through the internal electrode 21 to reach the ionization space 2b.

When the thermal electrons $e_A$ reach the inside of the ionization space 2b, the thermal electrons $e_A$ collide against the sample molecules A. Then, the sample molecules A are ionized by this electron impact, and the bindings in the molecules of the sample molecules A are cleaved to generate fragment ions $I_A$. The fragment ions $I_A$ are accelerated toward the quadrupole 4 (FIG. 1) by the electron lens forming electrodes 28a and 28b.

Note that, because the above-described electric field in the EI operation prevent the thermal electrons $e_A$ from jumping out of the external electrode 22, it is possible to prevent various problems which may be caused outside the external electrode 22 by the thermal electrons $e_A$, for example, problems such as electrification of the structural members. Further, at this time, when a PI operation by the electric discharge tube 29 which will be described later is performed at the same time, generated molecular ions $I_B$ are further decomposed into fragment ions $I_A$ usually by thermal electrons $e_A$ and secondary electrons $e_B$ generated due to ultraviolet light irradiation. However, by adjusting the emission of thermal electrons $e_A$ and the emission efficiency of secondary electrons $e_B$ due to ultraviolet light irradiation, it is possible to simultaneously detect fragment ions $I_A$ and molecular ions $I_B$ and to adjust the generating ratios thereof. In accordance therewith, it is possible to simultaneously obtain data on qualitative analysis such as the molecular mass and functional group.

[PI Operation by the Electric Discharge Tube 29]

Figure 4:
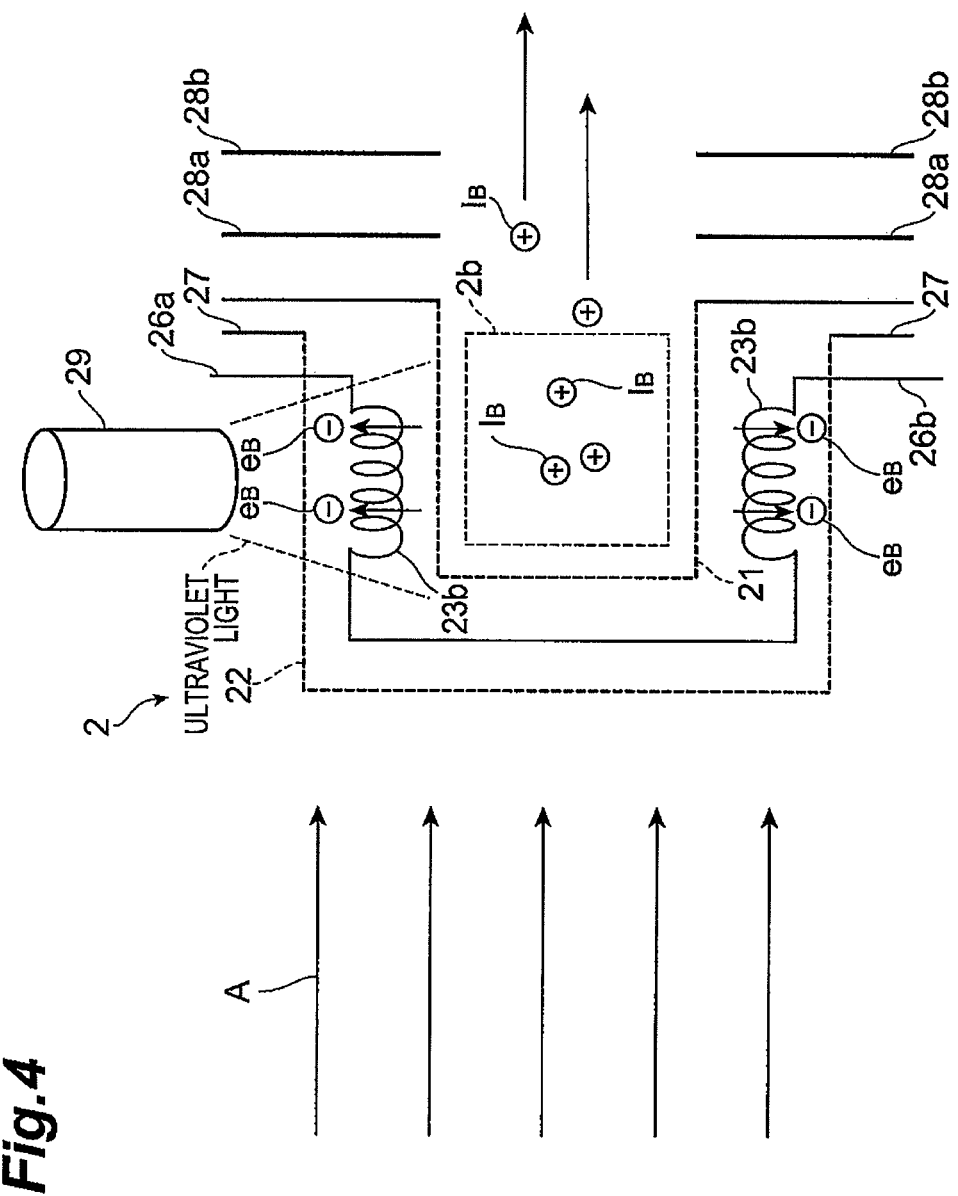
FIG. 4 is a diagram for explanation of a PI operation by an electric discharge tube among the operations of the ionizing device.

FIG. 4 is a diagram for explanation of a PI operation by the electric discharge tube 29 among the operations of the ionizing device 2. In a PI operation, due to the electric discharge tube 29 being supplied with electric power from the outside of the ionizing device 2, the electric discharge tube 29 irradiates the ionization space 2b with ultraviolet light. In accordance therewith, the sample molecules A are ionized to generate molecular ions parent ions) $I_B$. The molecular ions $I_B$ are introduced to the quadrupole 4 (FIG. 1) by the electron lens forming electrodes 28a and 28b.

Further, when the electric discharge tube 29 radiates ultraviolet light, secondary electrons $e_B$ are emitted from the internal electrode 21 and the filaments 23a and 23b due to the photo-electric effect. The secondary electrons $e_B$ are collected by the external electrode 22. That is, the relationship between an electric potential V1 of the internal electrode 21 and an electric potential V2 of the external electrode 22 at this time satisfies V1≤V2. In the case of V1<V2, an electric field reversed to that in an EI operation is formed between the internal electrode 21 and the external electrode 22. The secondary electrons $e_B$ are accelerated toward the external electrode 22 by this electric field. In this way, the secondary electrons $e_B$ are prevented from penetrating into the ionization space 2b, and are collected by the external electrode 22 (an electron collecting operation). Because the secondary electrons $e_B$ are collected by the external electrode 22, it is possible to prevent various problems which may be caused outside the ionization space 2b by the secondary electrons $e_B$, for example, problems such as electrification of the structural members. On the other hand, in the case of V1=V2, because the secondary electrons $e_B$ fly at only an initial speed, which do not reach energy making it possible to perform an EI operation in many cases, there is little influence on the molecular ions $I_B$. However, there is a possibility that the secondary electrons $e_B$ reach the ionization space 2b at an initial speed to react with the molecular ions $I_B$, and the content of the molecular ions $I_B$ is reduced.

[EI Operation by the Electric Discharge Tube 29]

Figure 5:
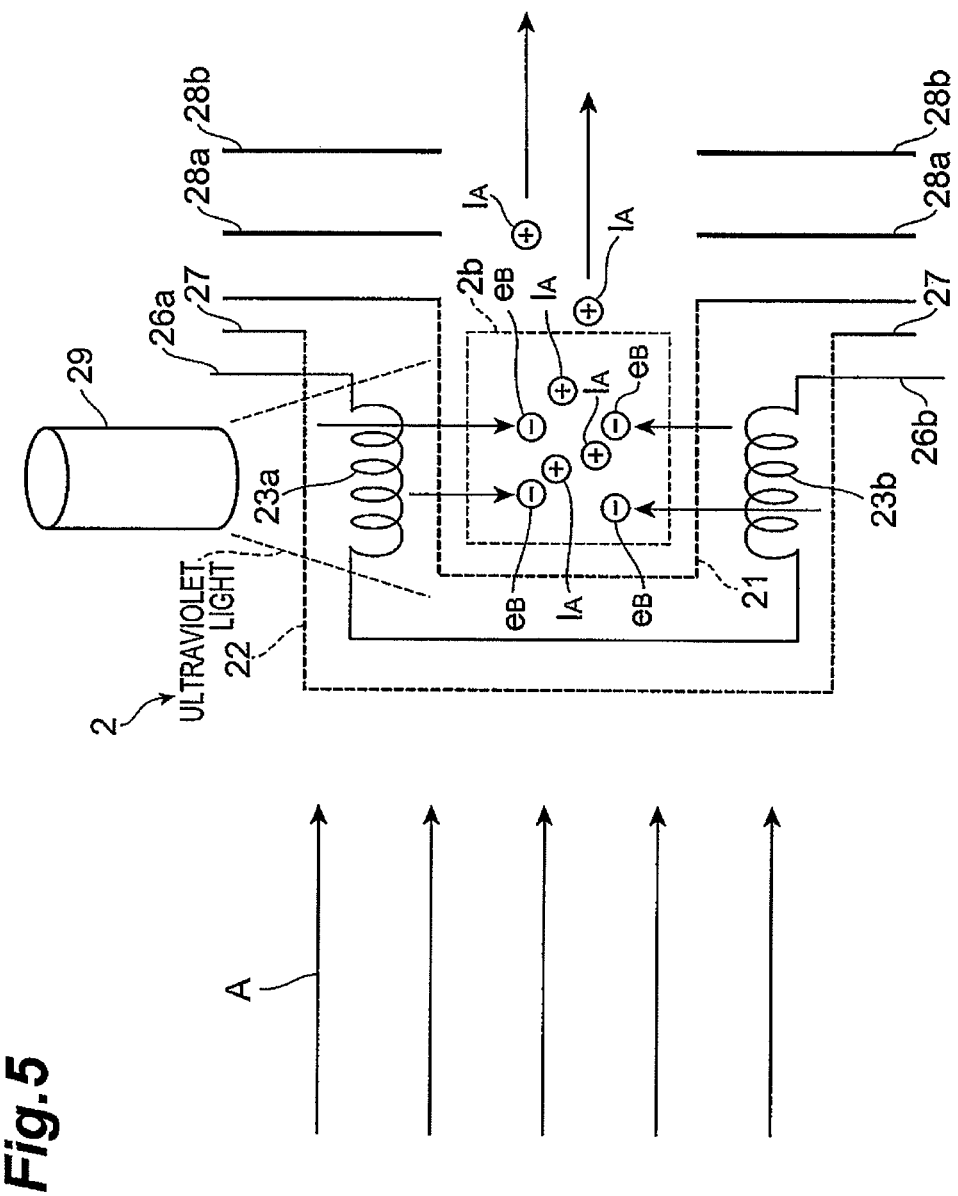
FIG. 5 is a diagram for explanation of an EI operation by using only the electric discharge tube without using emission of thermal electrons by the filaments among the operations of the ionizing device.

FIG. 5 is a diagram for explanation of an EI operation by using only the electric discharge tube 29 without using emission of thermal electrons by the filaments 23a and 23b among the operations of the ionizing device 2. In an EI operation, the electric discharge tube 29 irradiates the ionization space 2b with ultraviolet light. In accordance therewith, secondary electrons $e_B$ are emitted from the external electrode 22 and the filaments 23a and 23b due to the photo-electric effect (an electron emitting operation).

In this operation, different from the above-described PI operation, the relationship between an electric potential V1 of the internal electrode 21 and an electric potential V2 of the external electrode 22 is set to V1>V2. Further, when energization to the filaments 23a and 23b is maintained at an electric potential V3, the relationship of V1>V3≥V2 is to be satisfied. Note that a difference of potential between the electric potential V1 and the electric potential V2 (V3) is, for example, from 30V to 70V. In accordance therewith, an electric field which is the same as that in a case of an EI operation by the filaments 23a and 23b is formed between the internal electrode 21 and the external electrode 22. Accordingly, the secondary electrodes $e_B$ are accelerated toward the ionization space 2b to collide against the sample molecules A. Then, fragment ions $I_A$ are generated from the sample molecules A by this electron impact. In this way, the fragment ions $I_A$ generated inside the ionization space 2b are introduced to the quadrupole 4 (FIG. 1) by the electron lens forming electrodes 28a and 28b. Further, by adjusting a difference of potential and varying an acceleration voltage for the secondary electrons $e_B$ while satisfying the relationship of V1>V2, it is possible to generate not only fragment ions $I_A$, but also molecular ions $I_B$. That is, provided that a difference of potential between V1 and V2, i.e., an acceleration voltage is increased, it is possible to increase fragment ions $I_A$, and inversely, provided that an acceleration voltage is lowered, it is possible to increase molecular ions $I_B$.

Note that, in an EI operation by the electric discharge tube 29, because the filaments 23a and 23b merely function as secondary electron emission sources due to ultraviolet light irradiation, if a sufficient quantity of secondary electrons is obtained by the external electrode 22 or the like, the filaments 23a and 23b are unnecessary. On the other hand, secondary electrons $e_B$ may be emitted from the external electrode 22 and the filaments 23a and 23b, and at the same time, thermal electrons may be emitted from the filaments 23a and 23b. Further, a PI for the sample molecules A due to ultraviolet light irradiation is performed at the same time, and generated molecular ions $I_B$ are further decomposed into fragment ions $I_A$ usually by secondary electrons $e_B$. However, by adjusting the emission efficiency of secondary electrons $e_B$ due to ultraviolet light irradiation and the acceleration voltage thereof, it is possible to simultaneously detect fragment ions $I_A$ and molecular ions $I_B$ (EI and PI simultaneous operations) and to adjust the generating ratios thereof. In accordance therewith, it is possible to simultaneously obtain data on qualitative analysis such as the molecular mass and functional group.

The above description is premised on a case in which the respective operations are individually performed. However, a PI operation and an EI operation (including a case in which fragment ions $I_A$ and molecular ions $I_B$ are simultaneously generated) may be alternately performed at a predetermined time interval. For example, in a case in which a change over time of the sample is measured, when the sample within a time of changing over time is measured by a PI operation (or an EI operation) in the same way, and a same sample separately prepared is measured for the previous operation time by an EI operation (or a PI operation), there is a possibility that the sample environments for both the measurements are different from one another, and in this case, it is difficult to handle the information on the respective changes over time in the molecular ions and the fragment ions as changes under a same condition. In accordance therewith, when measurements for the respective operations are repeated alternately at short intervals within a time of changing over time, a change of the sample within the time is very slight, and the molecular ions and the fragment ions determined by the respective operations are considered as information on the same sample under the same environmental condition. Note that, in this case, the ionizing device 2 further includes a control unit (not shown) that controls power supply voltages to the electric discharge tube 29 and the filaments 23a and 23b, and a voltage applied to the external electrode 22 (or the internal electrode 21), and it is recommended that these operations be alternately performed while controlling a PI operation time and an EI operation time by the control unit.

The advantageous effects of the ionizing device 2 according to the present embodiment described above will be described. The ionizing device 2 of the present embodiment is capable of both EI and PI by including electron sources such as the filaments 23a and 23b emitting thermal electrons $e_A$ and electron emitting electrodes emitting secondary electrons $e_B$ (for which the external electrode 22 and the filaments 23a and 23b serve in the present embodiment), and the electric discharge tube 29 serving as a light emission means whose directivity is lower than that of a laser light. Moreover, because the electric discharge tube 29 has the directivity lower than that of a laser light, the electric discharge tube 29 is capable of uniformly irradiating the sample molecules A introduced more extensively as compared with a laser light source, with ultraviolet light. In accordance therewith, it is possible to improve the detection efficiency and detection sensitivity. Further, by using the electric discharge tube 29 as a light emission means, it is possible to form the device compact as compared with an ultraviolet laser light source. Further, by radiating ultraviolet light extensively, even when a spatial distribution of the introduced sample molecules is biased, it is possible to perform reliable ionization and obtain information well-rounded for the sample molecules, and it is possible to reduce the possibility that the ionized sample molecules react with neutral molecules or the like in an unirradiated region.

Further, as in the present embodiment, it is preferable that the ionizing device 2 includes the internal electrode 21 disposed between the electron sources and the ionization space 2b, and accelerates electrons (thermal electrons $e_A$ and secondary electrons $e_B$) emitted from the electron sources toward the ionization space 2b in an EI operation. In accordance therewith, it is possible to effectively have an electron impact on the sample molecules A.

Further, as in the present embodiment, it is preferable that the ionizing device 2 includes the external electrode 22 serving as an electron collecting electrode disposed outside the ionization space 2b. As described above, when the interior of the ionization chamber 2a is irradiated with ultraviolet light, secondary electrons $e_B$ are emitted from the structural members such as the filaments 23a and 23b and the internal electrode 21 due to the photo-electric effect. Then, when the secondary electrons $e_B$ penetrate into the ionization space 2b in a PI operation, the secondary electrons $e_B$ give an electron impact on the sample molecules A. Originally, PI is a method suitable for generating only molecular ions $I_B$ of the sample molecules A, which are decomposed into fragment ions due to too high ionization energy in EI, and therefore, it is preferable that fragment ions $I_A$ are generated as little as possible in PI. However, when the secondary electrons $e_B$ give an electron impact on the sample molecules A as described above, the sample molecules A are changed into fragment ions $I_A$.

In contrast thereto, in the ionizing device 2 of the present embodiment, the secondary electrons $e_B$ generated due to ultraviolet light irradiation can be collected by the external electrode 22. In accordance therewith, it is possible to prevent the secondary electrons $e_B$ from penetrating into the ionization space 2b, and reduce the emergence of fragment ions $I_A$ by a PI operation.

Further, as in the present embodiment, it is preferable that the ionizing device 2 includes the internal electrode 21 disposed between the external electrode 22 and the ionization space 2b, and accelerates the secondary electrons $e_B$ generated due to ultraviolet light irradiation toward the external electrode 22 in a PI operation. In accordance therewith, it is possible to more effectively prevent the secondary electrons $e_B$ from penetrating into the ionization space 2b.

Further, as in the present embodiment, it is preferable that the ionizing device 2 includes the external electrode 22 serving as an electron emitting electrode in which an electron source emits secondary electrons $e_B$ due to ultraviolet light irradiation from the electric discharge tube 29. In accordance therewith, it is possible to effectively give an electron impact in an EI operation by the electric discharge tube 29.

Further, as in the present embodiment, it is preferable that the ionizing device 2 includes the external electrode (the first electrode) 22 and the internal electrode (the second electrode) 21, and an electron emitting operation and an electron collecting operation by the external electrode 22 are switched in accordance with a relationship between an electric potential V2 of the external electrode 22 and an electric potential V1 of the internal electrode 21. In accordance therewith, both the electron emitting operation and the electron collecting operation are possible by the external electrode 22, the ionizing device 2 capable of efficiently performing both PI and EI can be made more compact.

Note that, when the electric discharge tube 29 is disposed inside the external electrode 22, it exercises an influence on an electric field formed by the external electrode 22 or the internal electrode 21 in some cases, and because an area in which the external electrode 22 can be utilized as a secondary electron emission source is decreased in an EI operation due to ultraviolet light irradiation, a quantity of secondary electrons to be emitted is decreased. Accordingly, it is preferable that the electric discharge tube 29 is disposed outside the external electrode 22 as in the present embodiment. Further, in order to enlarge a region irradiated with ultraviolet light, it is preferable that the electric discharge tube 29 is disposed to be separated from the ionization space 2b to some extent. Further, taking into consideration the radiation performance of the electric discharge tube 29, it is preferable that a part of the electric discharge tube 29 is exposed to the outside from the case 7. In particular, a resin component is used as a feeding portion such as a socket of the electric discharge tube 29 in some cases, and when the resin component is disposed inside the case 7, there is a risk that the analysis results will be influenced by a gas discharged from the resin. Accordingly, it is preferable that at least a resin feeding portion is disposed outside the case 7.

Further, in the present embodiment, the ionizing device 2 includes the one electric discharge tube 29. However, the ionizing device 2 may include a plurality of electric discharge tubes 29. In such a case, an intensity of irradiation may be enhanced by providing a plurality of electric discharge tubes 29 having the same characteristics, and different ionization energies may be provided to the sample molecules A by making the irradiation wavelength regions of the respective discharge tubes 29 different from one another. In particular, in a case in which the sample as an object to be analyzed includes several types of sample molecules A (a sample molecule group), provided that the irradiation wavelength regions of the respective discharge tubes 29 are different from one another, ionization for specific sample molecules A can be suitably performed by switching an irradiation wavelength region in accordance with an ionization potential which each of the sample molecules A as an object to be analyzed has.

(First Modification)

Figure 6:
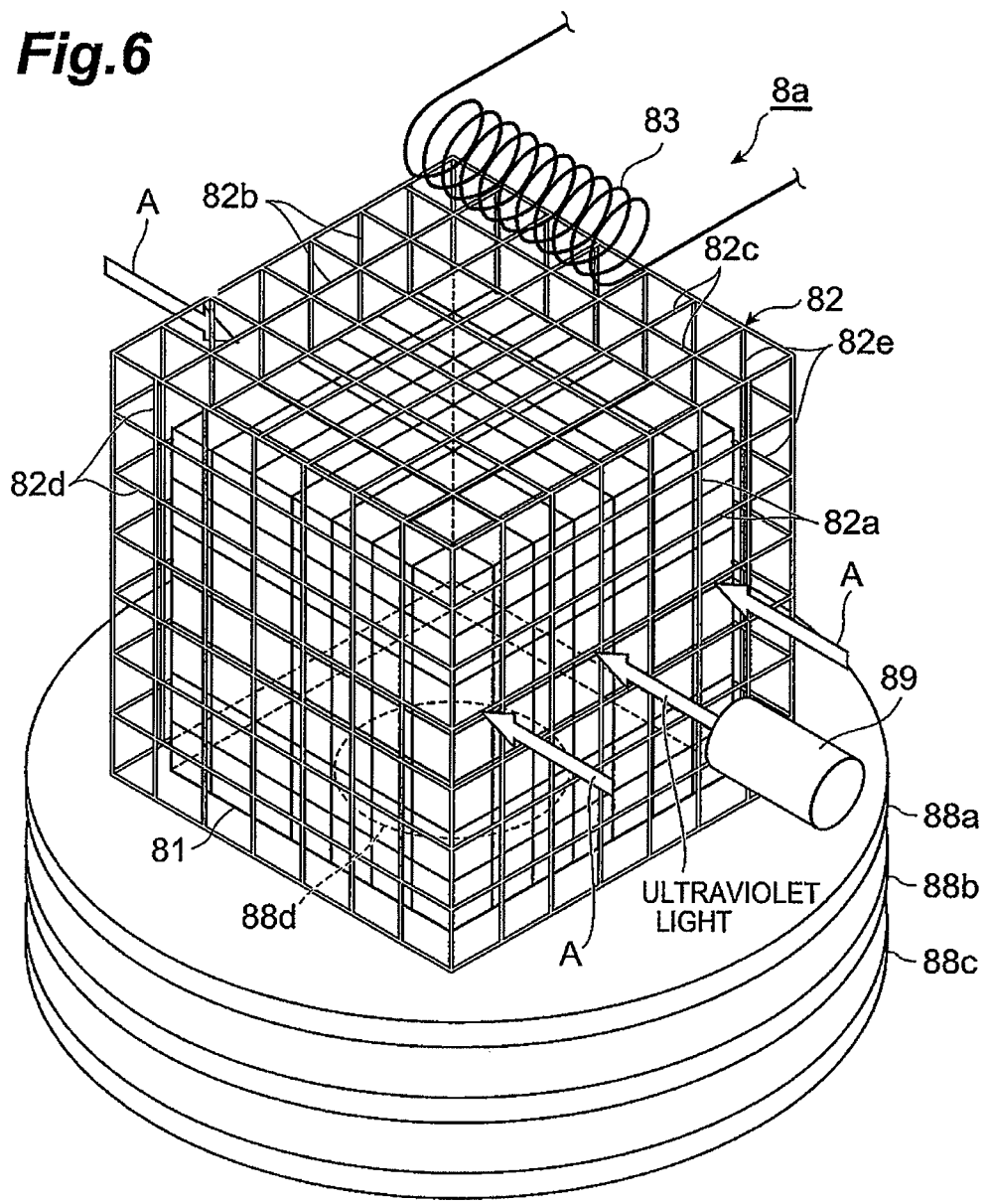
FIG. 6 is a perspective view showing a structure of an ionizing device according to a first modification.

FIG. 6 is a perspective view showing a structure of an ionizing device 8a according to a first modification of the above-described embodiment. The present embodiment is an example of an ionizing device capable of an EI operation, a PI operation, and EI and PI simultaneous operations by only an electric discharge tube serving as a light emission means without using filaments and the like as electron sources. In reference to FIG. 6, the ionizing device 8a according to the present modification includes an internal electrode 81, an external electrode 82, a heater for heating ionization chamber 83, electron lens forming electrodes 88a to 88c, an electric discharge tube 89, and an ionization chamber (not shown) housing these components.

The external electrode 82 is an electron collecting electrode and an electron emitting electrode in the present embodiment, and is operated in the same way as the external electrode 22 of the first embodiment. The external electrode 82 is composed of net-like conductive materials, and is formed into a rectangular parallelepiped box shape in which the net-like conductive materials are arranged on the other planes except for a plane facing the electron lens forming electrodes 88a to 88c. The interior of the external electrode 82 is a cavity, and the internal electrode 81 is disposed inside the external electrode 82. The external electrode 82 has a pair of net-like side face materials 82a and 82b facing each other, a pair of net-like side face materials 82d and 82e facing each other, which are disposed so as to be perpendicular to the side face materials 82a and 82b, and a net-like top face material 82c. Further, the internal electrode 81 is first and second accelerating electrodes in the present embodiment, and is operated in the same way as the internal electrode 21 of the first embodiment. The internal electrode 81 is formed into a rectangular parallelepiped box shape in which the net-like conductive materials are arranged on the other planes except for a plane facing the electron lens forming electrodes 88a to 88c, and the interior of the internal electrode 81 is an ionization space.

The sample molecules A are introduced and emitted from the side face materials 82a to 82e. Further, the electric discharge tube 89 is disposed at least at one side of the side face materials 82a and 82b (side face materials 82d and 82e), and in the present embodiment, the electric discharge tube 89 irradiates the ionization space in the internal electrode 81 with ultraviolet light via the side face material 82a. Further, the heater for heating ionization chamber 83 is disposed above the top face material 82c, and heats the respective electrodes in the ionization chamber as a heater.

The electron lens forming electrodes 88a to 88c are arrayed along the plane facing the top face material 82c in the external electrode 82. The electron lens forming electrodes 88a to 88c are formed into a disk form, and are arrayed in a direction perpendicular to the top face material 82c. Further, the electron lens forming electrodes 88a to 88c respectively have openings that communicate with one another (for example, an opening 88d of the electron lens forming electrode 88a) for allowing the ionized sample molecules A to pass through those. By applying a predetermined voltage to those, the electron lens forming electrodes 88a to 88c form an electric field by which ions are pulled out of the ionization space toward the quadrupole 4 (refer to FIG. 1).

In accordance with such a structure of the ionizing device 8a of the present modification, it is possible to suitably obtain an advantageous effect which is the same as that of the ionizing device 2 of the above-described embodiment. Note that the operations (the EI operation, the PI operation, and the EI and PI simultaneous operations) of the ionizing device 8a in the present modification are the same as those in the above-described embodiment, and detailed descriptions thereof will be omitted.

In the present modification, the entire planes of the external electrode 82 are formed net-like. However, planes through which the sample molecules A and ultraviolet light are introduced may be limited, and the other planes may be formed of plate-like members. For example, when only the side face material 82a is formed net-like, and the other planes are formed of plate-like members, it is possible to increase a quantity of secondary electrons to be emitted from the external electrode 82 due to ultraviolet light irradiation, and effectively give an electron impact on the sample molecules A in an EI operation and EI and PI simultaneous operations. Further, in this case, some of the plate-like planes may be opened to be used for discharging the sample. Further, one plane forming the external electrode 82 may be formed of a plate-like member in which only a region required for introducing the sample molecules A and ultraviolet light is formed of a net-like member. In accordance therewith, it is possible to realize introduction of the sample molecules A and ultraviolet light, and an increase in secondary electrons to be emitted in a balance manner.

(Second Modification)

Figure 7:
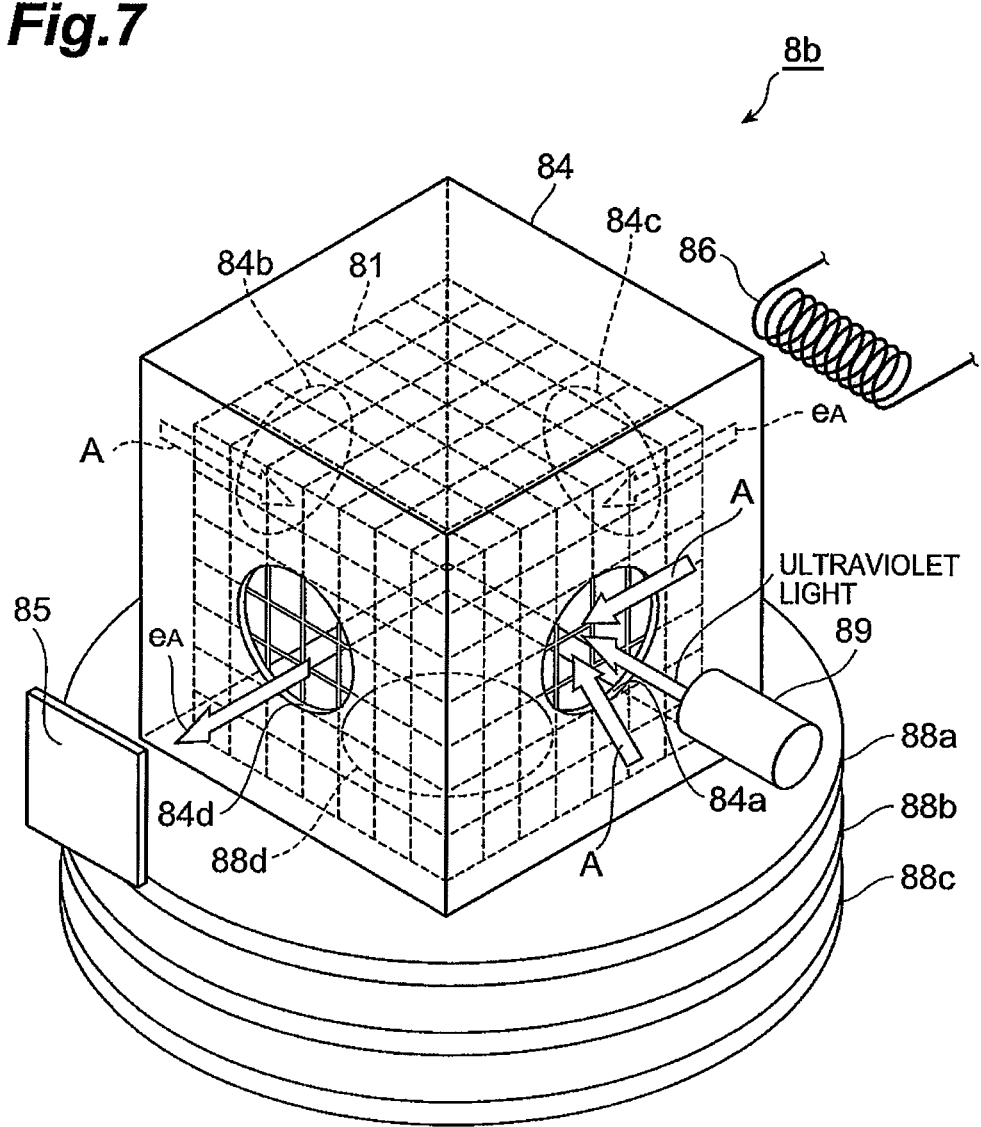
FIG. 7 is a perspective view showing a structure of an ionizing device according to a second modification.

FIG. 7 is a perspective view showing a structure of an ionizing device 8b according to a second modification of the above-described embodiment. In reference to FIG. 7, the ionizing device 8b according to the present modification includes the internal electrode 81, an external electrode 84, a collector electrode 85, a filament 86, the electron lens forming electrodes 88a to 88c, the electric discharge tube 89, and an ionization chamber (not shown) housing these components. Note that, the structures and the operations of the internal electrode 81 and the electron lens forming electrodes 88a to 88c among these are the same as those in the above-described first modification.

The external electrode 84 of the present modification is formed into a rectangular parallelepiped box shape without a side face of the electron lens forming electrodes 88a to 88c. The interior of the external electrode 84 is a cavity, and the internal electrode 81 is disposed inside the external electrode 84. The external electrode 84 has sample introduction ports 84a and 84b formed in a pair of side faces facing each other. Further, the external electrode 84 has electron passage ports 84c and 84d formed in a pair of side faces different from the pair of side faces in which the sample introduction ports 84a and 84b are formed. Note that the sample introduction ports 84a and 84b and the electron passage ports 84c and 84d may be formed net-like.

The sample molecules A are introduced and emitted from the sample introduction ports 84a to 84d. The electric discharge tube 89 is disposed at a side of the sample introduction port 84a, and the electric discharge tube 89 irradiates the ionization space in the internal electrode 81 with ultraviolet light via the sample introduction port 84a from the electric discharge tube 89. The filament 86 is disposed at a side of the electron passage port 84c. The collector electrode 85 is disposed at a side of the electron passage port 84d. The thermal electrons $e_A$ pass through the electron passage port 84c to be introduced to the ionization space in the internal electrode 81. The thermal electrons $e_A$ passing through the ionization space without having an electron impact on the sample molecules A pass through the electron passage port 84d to be collected by the collector electrode 85.

In accordance with the structure of the ionizing device 8b of the present modification as well, it is possible to suitably obtain an advantageous effect which is the same as that of the ionizing device 2 of the above-described embodiment. Further, in accordance with the ionizing device 8b of the present modification, because an area of the external electrode 84 can be enlarged as compared with that in the above-described first modification, it is possible to further increase a quantity of secondary electrons to be emitted from the external electrode 84 due to irradiation of vacuum ultraviolet light VUV.

(Third Modification)

Figure 8:
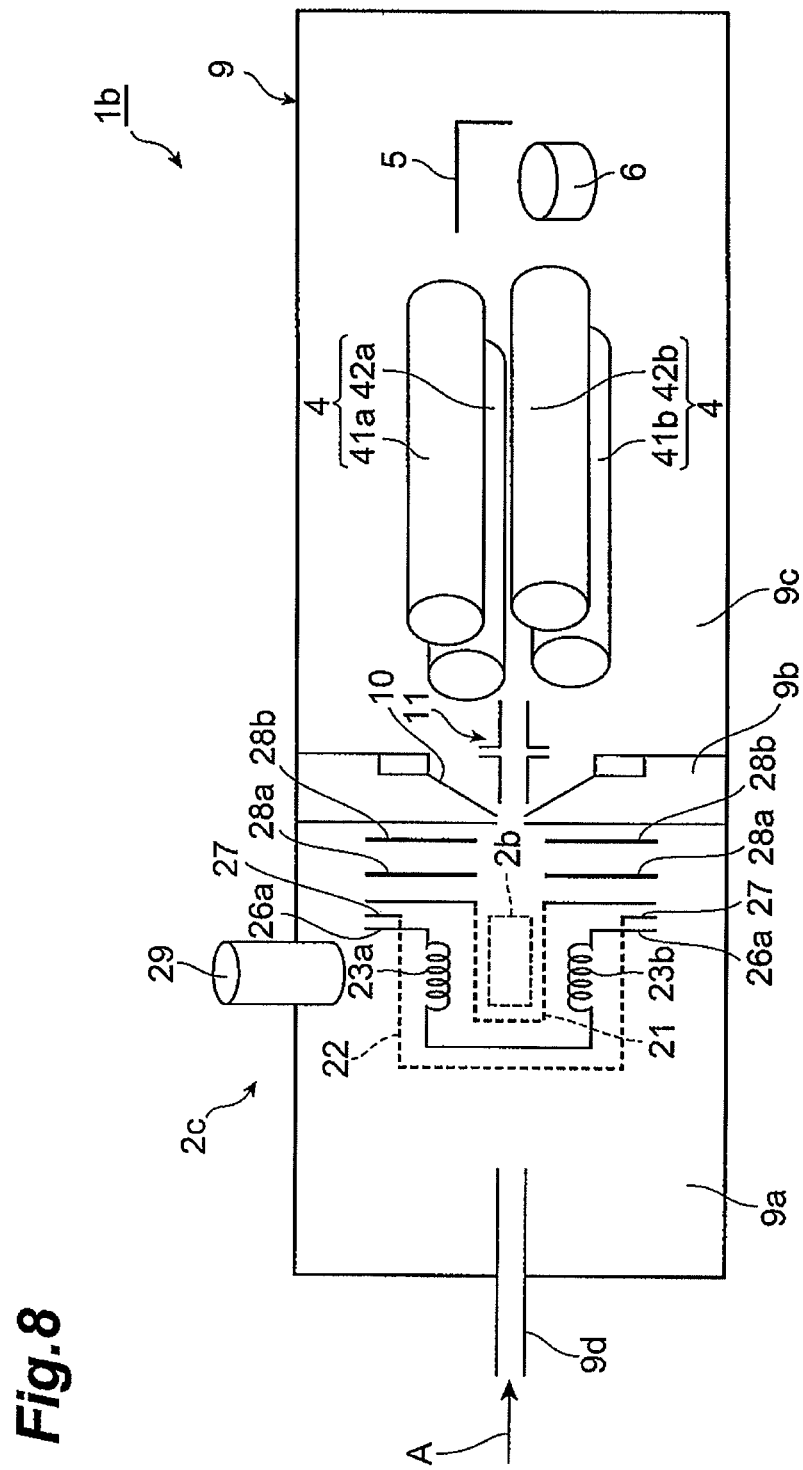
FIG. 8 is a diagram showing an ionizing device according to a third modification, and a structure of a mass analyzer having the ionizing device.

FIG. 8 is a diagram showing an ionizing device 2c according to a third modification of the above-described embodiment, and a mass analyzer 1b having the ionizing device 2c. A point of difference between the above-described embodiment and the present modification is the shape of the case of the mass analyzer 1b. That is, a case 9 of the present modification has an ionization chamber 9a, a sample analysis chamber 9c, an adjustment chamber 9b provided between the ionization chamber 9a and the sample analysis chamber 9c.

The ionization chamber 9a forms a part of the ionizing device 2c. That is, the internal electrode 21, the external electrode 22, the filaments 23a and 23b, and the electron lens forming electrodes 28a and 28b of the ionizing device 2c are disposed inside the ionization chamber 9a. Then, the sample molecules A are introduced into the interior of the ionization chamber 9a via a sample introduction port 9d provided in the ionization chamber 9a. A sample introduction portion is limited by the sample introduction port 9d to introduce the sample molecules A in the vicinity of the ionization space 2b. Therefore, the sample molecules A are introduced to the inside of the ionization space 2b in a more concentrated manner, which makes it possible to perform more efficient ionization. When the ionizing device 2c performs an EI operation or EI and PI simultaneous operations, the pressure inside the ionization chamber 9a is kept at a vacuum. Further, the ionizing device 2c performs a PI operation, by executing differential evacuation of the ionization chamber 9a, the adjustment chamber 9b, and the sample analysis chamber 9c, the ionization chamber 9a can be released at an atmosphere pressure or to an extent at an atmosphere pressure.

A skimmer 10 is installed in the adjustment chamber 9b. The skimmer 10 is disposed so as to correspond to the openings of the electron lens forming electrodes 28a and 28b of the ionizing device 2c, and keeps a differential pressure between the ionization chamber 9a and the sample analysis chamber 9c. Further, the quadrupole 4, the deflector 5, the detector 6, and an electron lens forming electrode 11 are disposed inside the sample analysis chamber 9c. The electron lens forming electrode 11 is disposed between the skimmer 10 in the adjustment chamber 9b and the quadrupole 4, and converges ions passing through the skimmer 10 to the quadrupole 4.

In the case of an EI operation or EI and PI operations, because an electron impact is made on the sample molecules A by thermal electrons and secondary electrons, it is necessary to keep the interior of the ionization chamber 9a at a vacuum. On the other hand, in the case of a PI operation, because the sample molecules A are ionized by ultraviolet light from the electric discharge tube 29, the operation is possible even under the atmosphere pressure. However, in that case, in order to keep the sample analysis chamber 9c at a vacuum, in addition to the evacuation in the sample analysis chamber 9c, the ionization chamber 9a and the adjustment chamber 9b are preferably evacuated. As in the present modification, provided that a mechanism to keep a differential pressure between the both chambers by separating the ionization chamber 9a and the sample analysis chamber 9c of the ionizing device 2c is provided, it is possible to more suitably keep the sample analysis chamber 9c at a vacuum. Note that, at the time of evacuating excess samples in the ionization chamber 9a, the evacuation in the adjustment chamber 9b may be utilized, or another opening for evacuating samples may be provided in the ionization chamber 9a.

(Fourth Modification)

Figure 9:
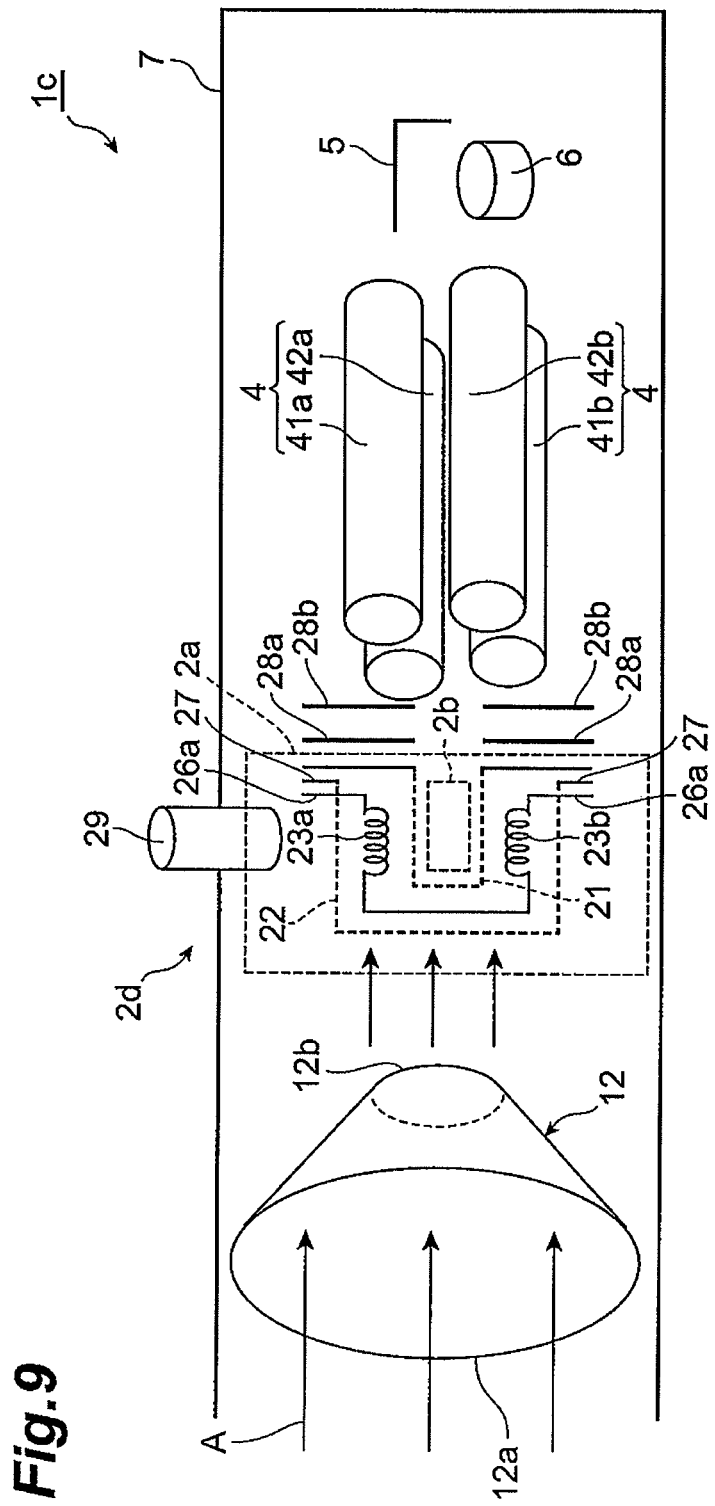
FIG. 9 is a diagram showing an ionizing device according to a fourth modification, and a structure of a mass analyzer having the ionizing device.

FIG. 9 is a diagram showing an ionizing device 2d according to a fourth modification of the above-described embodiment, and a structure of a mass analyzer 1c having the ionizing device 2d. A point of difference between the above-described embodiment and the present modification is the presence or absence of a rectifier member. That is, the ionizing device 2d of the present modification includes a rectifier member 12 to efficiently introduce the sample molecules A.

The rectifier member 12 of the present modification is formed into a truncated cone and tubular form, and one end and the other end thereof are respectively a sample introduction port 12a and a sample discharge port 12b. The sample discharge port 12b is made narrower than the sample introduction port 12a, and is disposed so as to be directed to the ionization space 2b. The sample molecules A introduced from the sample introduction port 12a are rectified by the rectifier member 12, and are efficiently introduced into the ionization space 2b. The ionizing device 2d preferably includes the rectifier member 12 as in the present modification. In accordance therewith, the utilization efficiency of the sample molecules A is improved, which makes it possible to generate more ions.

The ionizing device according to the present invention is not limited to the above-described embodiment and modifications, and other various modifications are also possible. For example, in the above-described embodiment, the external electrode serves as both the electron emitting electrode that emits electrons due to ultraviolet light irradiation from the electric discharge tube and the electron collecting electrode. However, the electron emitting electrode and the electron collecting electrode may be separately provided. Further, a plurality of accelerating electrodes may be provided, and those may serve as an electron collecting electrode and an electron emitting electrode. Further, as an electrode source, a cold cathode may be used. Further, a light emission means may be, not only the electric discharge tube, but also a device capable of radiating ultraviolet light whose directivity is lower than that of a laser light, for example, an ultraviolet light source that emits ultraviolet light by making an electron beam from an electron beam tube collide against a target or a gaseous body.

The invention claimed is:

1. An ionizing device comprising:
    an ionization chamber having an ionization space for ionizing sample molecules;
    an electron source to have an electron impact on the sample molecules in the ionization space, to ionize the sample molecules;
    light emission means for irradiating the sample molecules in the ionization space with ultraviolet light whose directivity is lower than that of a laser light, to ionize the sample molecules; and
    further comprising an electron collecting electrode, which is disposed in a space between the light emission means and the ionization space, to collect electrons generated due to the ultraviolet light irradiation in the ionization space,
    wherein the electron collecting electrode is disposed to surround the ionization space.

2. The ionizing device according to claim 1, wherein the light emission means is an electric discharge tube.

3. The ionizing device according to claim 1, further comprising a first accelerating electrode, which is disposed between the electron source and the ionization space, to accelerate electrons from the electron source toward the ionization space.

4. The ionizing device according to claim 1, wherein the electron source includes an electron emitting electrode that emits electrons due to the ultraviolet light irradiation from the light emission means.

5. The ionizing device according to claim 4, wherein the electron emitting electrode has a base portion and a coating portion that coats the base portion, and a secondary electron emission efficiency of the coating portion is higher than a secondary electron emission efficiency of the base portion.

6. The ionizing device according to claim 1, further comprising a rectifier member that rectifies the sample molecules toward the ionization space.

7. The ionizing device according to claim 1, wherein the light emission means is disposed without facing to an aperture of the ionization chamber through which the ions are picked up.

8. An ionizing device comprising:
    an ionization chamber having an ionization space for ionizing sample molecules;
    an electron source to have an electron impact on the sample molecules in the ionization space, to ionize the sample molecules; and
    light emission means for irradiating the sample molecules in the ionization space with ultraviolet light whose directivity is lower than that of a laser light, to ionize the sample molecules,
    further comprising an electron collecting electrode, which is disposed outside the ionization space, to collect electrons generated due to the ultraviolet light irradiation in the ionization space, and
    further comprising a second accelerating electrode, which is disposed between the electron collecting electrode and the ionization space, to accelerate electrons generated due to the ultraviolet light irradiation in the ionization space toward the electron collecting electrode.

9. The ionizing device according to claim 8, wherein the light emission means is an electric discharge tube.

10. The ionizing device according to claim 8, further comprising a first accelerating electrode, which is disposed between the electron source and the ionization space, to accelerate electrons from the electron source toward the ionization space.

11. The ionizing device according to claim 8 comprising a first accelerating electrode, which is disposed between the electron source and the ionization space, to accelerate electrons from the electron source toward the ionization space, wherein the first accelerating electrode serves as the second accelerating electrode.

12. The ionizing device according to claim 8, wherein the electron source includes an electron emitting electrode that emits electrons due to the ultraviolet light irradiation from the light emission means.

13. The ionizing device according to claim 12, wherein the electron emitting electrode has a base portion and a coating portion that coats the base portion, and a secondary electron emission efficiency of the coating portion is higher than a secondary electron emission efficiency of the base portion.

14. The ionizing device according to claim 8, further comprising a rectifier member that rectifies the sample molecules toward the ionization space.

15. An ionizing device comprising:
an ionization chamber having an ionization space for ionizing sample molecules;
light emission means for irradiating the sample molecules in the ionization space with ultraviolet light whose directivity is lower than that of a laser light, to ionize the sample molecules;
a first electrode which is disposed outside the ionization space, the first electrode performs an electron emitting operation for emitting electrons due to the ultraviolet light irradiation from the light emission means to have an electron impact on the sample molecules in the ionization space, and an electron collecting operation for collecting electrons generated in the ionization chamber due to the ultraviolet light irradiation; and
a second electrode which is disposed between the first electrode and the ionization space, wherein
the electron emitting operation and the electron collecting operation in the first electrode are switched in accordance with a relationship between electric potentials of the first electrode and the second electrode.

16. The ionizing device according to claim 15, wherein the light emission means is an electric discharge tube.

17. The ionizing device according to claim 15, wherein the electron emitting operation and the electron collecting operation in the first electrode are alternately performed while controlling operating times of the respective operations.

18. The ionizing device according to claim 15, further comprising a rectifier member that rectifies the sample molecules toward the ionization space.

19. An ionizing device comprising:
an ionization chamber having an ionization space for ionizing sample molecules;
an electron source to have an electron impact on the sample molecules in the ionization space, to ionize the sample molecules; and
light emission means for irradiating the sample molecules in the ionization space with ultraviolet light whose directivity is lower than that of a laser light, to ionize the sample molecules, and
a rectifier member that rectifies the sample molecules toward the ionization space,
wherein the electron source includes an electron emitting electrode that emits electrons due to the ultraviolet light irradiation from the light emission means.

20. The ionizing device according to claim 19, wherein the light emission means is an electric discharge tube.

21. The ionizing device according to claim 19, further comprising a first accelerating electrode, which is disposed between the electron source and the ionization space, to accelerate electrons from the electron source toward the ionization space.

22. The ionizing device according to claim 19, further comprising an electron collecting electrode, which is disposed outside the ionization space, to collect electrons generated due to the ultraviolet light irradiation in the ionization space.

23. The ionizing device according to claim 19, wherein the electron emitting electrode has a base portion and a coating portion that coats the base portion, and a secondary electron emission efficiency of the coating portion is higher than a secondary electron emission efficiency of the base portion.

* * * * *

UNITED STATES PATENT AND TRADEMARK OFFICE
CERTIFICATE OF CORRECTION

PATENT NO.        : 8,592,779 B2
APPLICATION NO.   : 12/281069
DATED             : November 26, 2013
INVENTOR(S)       : Matsuura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this
Twenty-second Day of September, 2015

Michelle K. Lee
*Director of the United States Patent and Trademark Office*